(12) United States Patent  (10) Patent No.: US 9,327,124 B2
Tass  (45) Date of Patent: May 3, 2016

(54) APPARATUS AND METHOD FOR CALIBRATING INVASIVE ELECTRIC DESYNCHRONIZING NEUROSTIMULATION

(71) Applicant: Forschungszentrum Juelich GmbH, Juelich (DE)

(72) Inventor: Peter Alexander Tass, Juelich (DE)

(73) Assignee: Forschungszentrum Juelich GmbH, Juelich (DE)

( * ) Notice: Subject to any disclaimer, the term of this patent is extended or adjusted under 35 U.S.C. 154(b) by 0 days.

(21) Appl. No.: 14/375,589

(22) PCT Filed: Feb. 7, 2013

(86) PCT No.: PCT/EP2013/052453
§ 371 (c)(1),
(2) Date: Jul. 30, 2014

(87) PCT Pub. No.: WO2013/117656
PCT Pub. Date: Aug. 15, 2013

(65) Prior Publication Data
US 2015/0018898 A1  Jan. 15, 2015

(30) Foreign Application Priority Data
Feb. 8, 2012 (DE) .......................... 10 2012 002 437

(51) Int. Cl.
*A61N 1/36* (2006.01)
*A61N 1/05* (2006.01)

(52) U.S. Cl.
CPC ........ *A61N 1/36167* (2013.01); *A61N 1/36064* (2013.01); *A61N 1/36067* (2013.01);
(Continued)

(58) Field of Classification Search
CPC ............ A61N 1/0534; A61N 1/36067; A61N 1/36135; A61N 1/36139; A61N 1/36185; A61B 5/0476; A61B 5/048; A61B 5/4064; A61B 5/4082
See application file for complete search history.

(56) References Cited

U.S. PATENT DOCUMENTS 6,597,954 B1  7/2003  Pless
2006/0212089 A1*  9/2006  Tass .................... A61N 1/36017
607/45

(Continued)

FOREIGN PATENT DOCUMENTS

DE  10 2008 052 078 A1  4/2010
JP  2006/523474 A  10/2006
(Continued)

OTHER PUBLICATIONS

International Search Report for PCT/EP2013/052453, dated Aug. 8, 2013.
(Continued)

*Primary Examiner* — Eugene Wu
(74) *Attorney, Agent, or Firm* — Arent Fox LLP

(57) ABSTRACT

The invention relates to an apparatus for stimulating neurons having a pathological synchronous and oscillatory neural activity, the apparatus including a stimulation unit having a plurality of stimulation contacts to stimulate neurons in a patients brain and/or spinal cord with electric stimuli, a measurement unit for recording test signals that represent a neural activity of the stimulated neurons, and a control and analysis unit. Furthermore, the stimulation contacts of the stimulation unit apply stimuli, and the control and analysis unit selects the stimulation contacts, the stimuli of which cause the phase of the pathological synchronous and oscillatory neural activity of the stimulated neurons to be reset. The selected stimulation contacts then apply phase-resetting stimuli with a time delay, and the control and analysis unit verifies whether the pathological synchronous and oscillatory neural activity of the stimulated neurons is suppressed by said time-delayed stimuli.

10 Claims, 8 Drawing Sheets

(52) U.S. Cl.
CPC ........ *A61N1/36139* (2013.01); *A61N 1/36185* (2013.01); *A61N 1/0534* (2013.01); *A61N 1/36082* (2013.01)

(56) References Cited

U.S. PATENT DOCUMENTS

| | | | |
|---|---|---|---|
| 2008/0027514 A1* | 1/2008 | DeMulling | A61N 1/36185 607/60 |
| 2010/0100153 A1* | 4/2010 | Carlson | A61N 1/0529 607/45 |
| 2010/0168816 A1 | 7/2010 | Tass et al. | |
| 2011/0201977 A1 | 8/2011 | Tass | |
| 2011/0264165 A1* | 10/2011 | Molnar | A61N 1/36185 607/45 |
| 2013/0245713 A1 | 9/2013 | Tass | |

FOREIGN PATENT DOCUMENTS

| | | |
|---|---|---|
| WO | WO-03/043690 A1 | 5/2003 |
| WO | WO-2008/109508 A2 | 9/2008 |
| WO | WO-2011/127917 A2 | 10/2011 |

OTHER PUBLICATIONS

P.A. Tass; "A model of desynchronizing deep brain stimulation with a demand-controlled coordinated reset of neural subpopulations"; Biological Cybernetics 89, 2003, pp. 81-88.

A.M. Kuncel and W.M. Grill; "Selection of stimulus parameters for deep brain stimulation"; Clinical Neurophysiology 115, 2004, pp. 2431-2441.

U. Gimsa et al.; "Matching geometry and stimulation parameters of electrodes for deep brain stimulation experiments—Numerical considerations"; Journal of Neuroscience Methods 150, 2006, pp. 212-227.

P. A. Tass; "Stochastic phase of two coupled phase oscillators stimulated at different times"; Physical Review E 67, 2003, pp. 051902-1 to 051902-15.

N.E. Huang et al.; "The empirical mode decomposition and the Hilbert spectrum for nonlinear and non-stationary time series analysis"; Proceedings of Royal Society of London Series A, 1998, vol. 454, pp. 903-995.

N.E. Huang et al.; "A confidence limit for the empirical mode decomposition and Hilbert spectral analysis"; Proceedings of the Royal Society of London Series A, 2003, vol. 459, pp. 2317-2345.

* cited by examiner

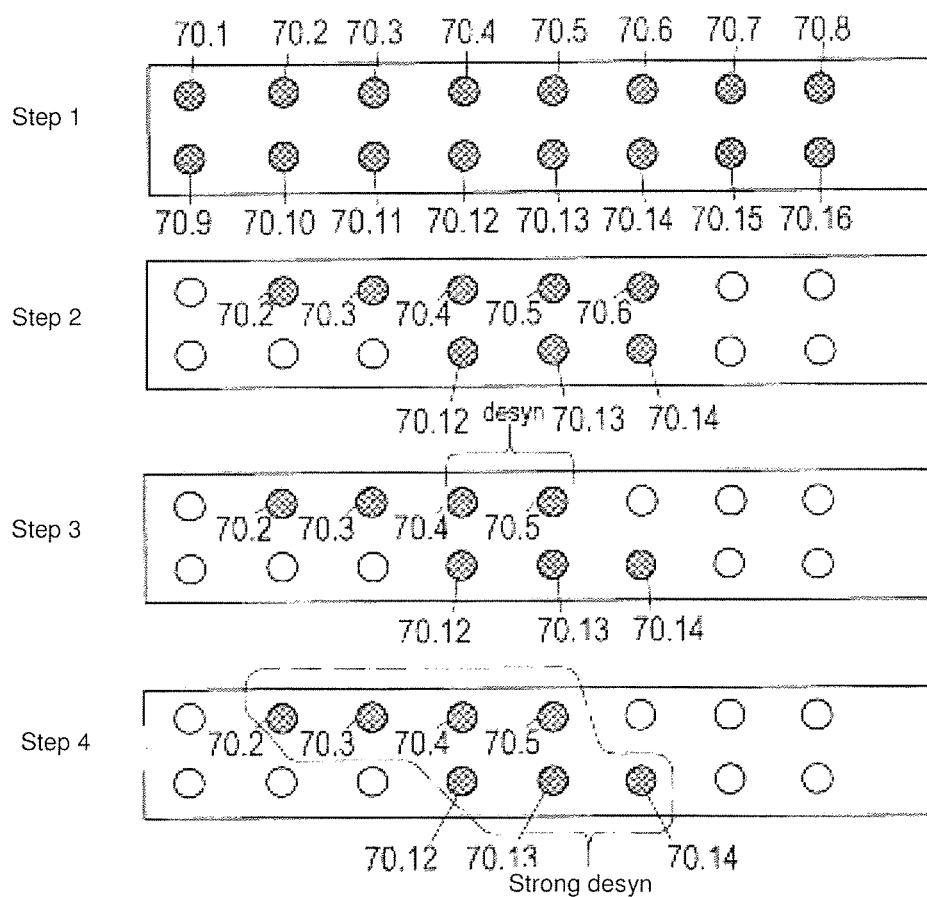

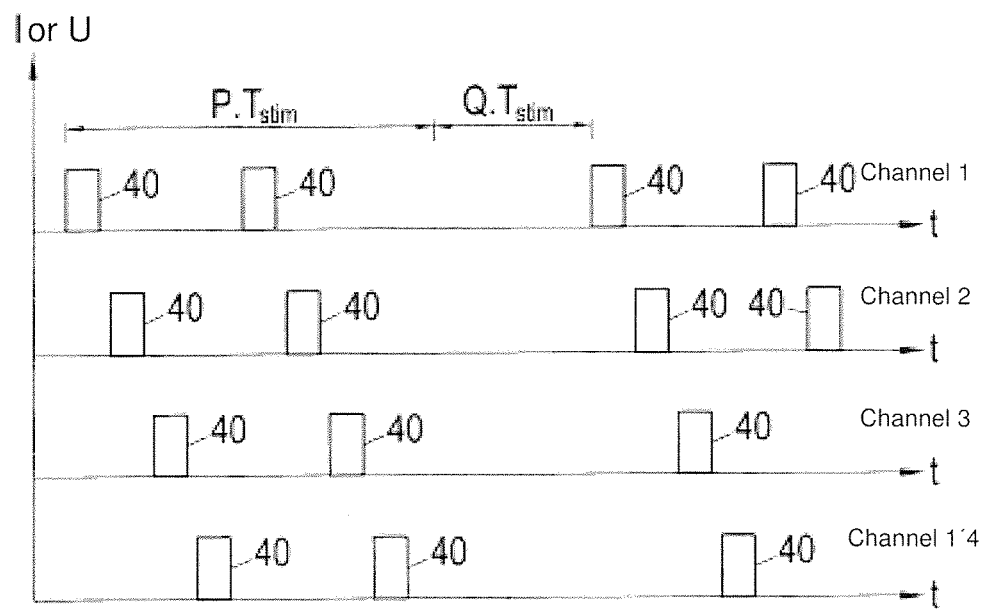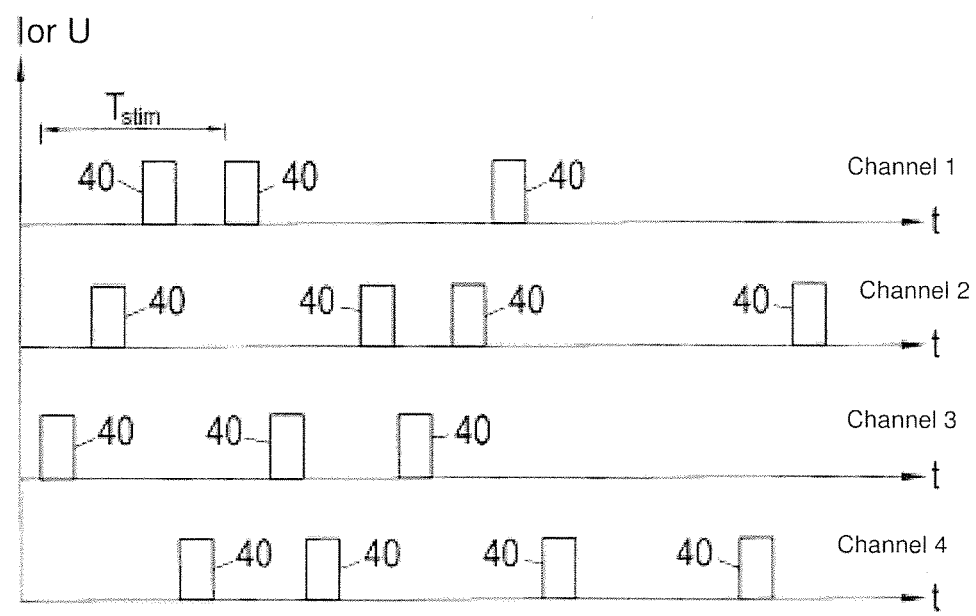

APPARATUS AND METHOD FOR CALIBRATING INVASIVE ELECTRIC DESYNCHRONIZING NEUROSTIMULATION

TECHNICAL FIELD

The invention relates to an apparatus and to a method for calibrating invasive, electrical and desynchronizing neurostimulation.

BACKGROUND

Nerve cell assemblies in circumscribed regions of the brain are pathologically, e.g. excessively synchronously, active in patients with neurological or psychiatric diseases such as Parkinson's disease, essential tremor, dystonia or obsessive compulsive disorders. In this case, a large number of neurons synchronously form action potentials, i.e. the participating neurons fire excessively synchronously. In a healthy person, in contrast, the neurons fire with a different quality, i.e. in an uncorrelated manner, in these brain areas.

Stimulation techniques have been developed for treating such diseases which directly counteract pathologically synchronous neural activity. In particular the coordinated reset (CR) stimulation is in this respect characterized by great therapeutic effectiveness and reliability (cf. e.g. "A model of desynchronizing deep brain stimulation with a demand-controlled coordinated reset of neural subpopulations" by P. A. Tass, published in Biol. Cybern. 89, 2003, pages 81 to 88). In order to directly develop a desynchronizing effect in circumscribed target zones of the brain, electrodes (e.g. deep electrodes) are implanted in these target zones and/or in fibrous zones associated therewith. It is of central importance for the effectiveness of the CR stimulation that the different stimulation contacts lie in the neural population to be stimulated and/or in fibrous zones associated therewith. Optimum CR stimulation can only be carried out using at least two stimulation contacts, more would be better (e.g. four and more). The optimum stimulation contacts are in particular to be selected in accordance with their actual stimulation effect on the neural population to be desynchronized. To date, there is no automatically functioning process which uses objective measurement parameters for selecting the N optimum stimulation contacts from a larger number M (where M>N) of stimulation contacts. The selection of suitable stimulation contacts and of the associated parameters (e.g. the stimulation amplitude) rather takes place by time-consuming trial and error. This trial and error process does not guarantee the optimum effectiveness of the invasive CR therapy since, on the one hand, (in particular with a larger number of stimulation contacts) not all possible stimulation sites in the brain are systematically examined and, on the other hand, the patients are stressed by long examinations so that the cooperation of the patients naturally suffers and the results of the testing become worse.

SUMMARY

It is the underlying object of the invention to provide an apparatus and a method which allow a calibration of the stimulation parameters independent of the examiner, carried out automatically and on an electrophysiological basis. This calibration should in particular make it possible (i) to carry out the therapy effectively; (ii) to avoid side effects; and (iii) to make the examination to be carried out for the parameter setting as short, practical and tolerable as possible for the patient.

The object underlying the invention is satisfied by the features of the independent claims. Advantageous further developments and aspects of the invention are set forth in the dependent claims.

The invention will be described in more detail in the following in an exemplary manner with reference to an embodiment and to the drawings.

BRIEF DESCRIPTION OF THE DRAWINGS

FIG. 9 a flowchart to illustrate the calibration for an electrode with circle-shaped stimulation contacts;

FIG. 10 a schematic representation of a variant of the CR stimulation;

FIG. 11 a schematic representation of a further variant of the CR stimulation.

DETAILED DESCRIPTION

Figure 1:
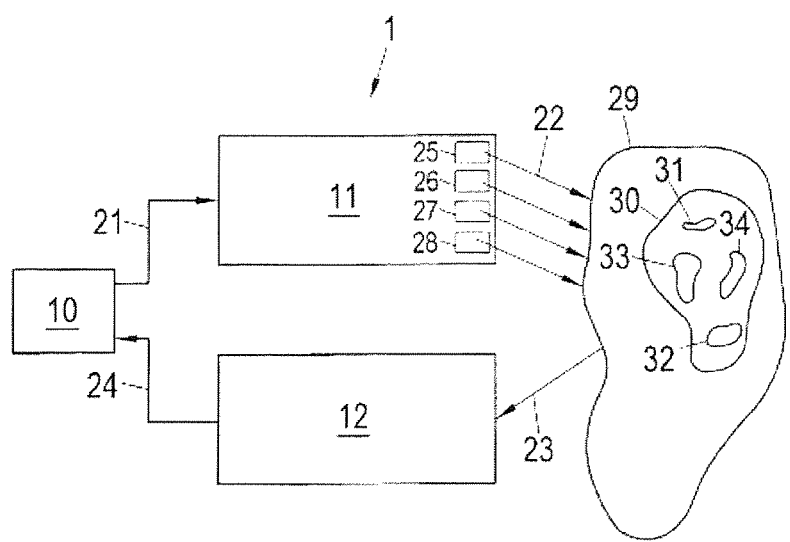
FIG. 1 a schematic representation of an apparatus for invasive, electrical and desynchronizing neurostimulation during operation.

An apparatus 1 for calibrating the stimulation parameters of an invasive, electrical and desynchronizing neurostimulation is shown in FIG. 1. The apparatus 1 comprises a control and analysis unit 10, a stimulation unit 11 and a measuring unit 12. During the operation of the apparatus 1, the control and analysis unit 10 inter alia carries out a control of the stimulation unit 11. For this purpose, the control and analysis unit 10 generates control signals 21 which are received by the stimulation unit 11. The stimulation unit 11 is surgically implanted in the body of the patient and generates electrical stimuli 22 on the basis of the control signals 21 which are delivered to the brain and/or to the spinal cord of the patient. The control and analysis unit 10 and/or the measuring unit 12 can be non-invasive units, i.e. they are located outside the body of the patient during the operation of the apparatus 1 and are not surgically implanted in the body of the patient.

The stimulation effect achieved by the electrical stimuli 22 is monitored with the aid of the measuring unit 12. The measuring unit 12 takes up one or more measured signals measured at the patient, converts them as required into electrical signals 24 and supplies them to the control and analysis unit 10. The neural activity in the stimulated target zone or in a zone associated with the target zone can in particular be measured by means of the measuring unit 12, with the neural activity of this zone correlating sufficiently closely with the neural activity of the target zone. The control and analysis unit 10 processes the signals 24, e.g. the signals 24 can be amplified and/or filtered, and analyzes the processed signals 24. The control and analysis unit 10 in particular controls the stimulation unit 11 with reference to the results of this analysis. The control and analysis unit 10 can include e.g. a processor (e.g. a microcontroller) for carrying out its work.

The stimulation unit 11 can e.g. be a brain pacemaker and has one or more implantable electrodes, e.g. deep electrodes, as well as optionally connection cables connected therebetween. The electrodes of the stimulation unit 11 typically comprise an insulated electrode shaft and a plurality of stimulation contacts (or stimulation contact surfaces) which have been introduced into the electrode shaft. Four stimulation contacts 25, 26, 27 and 28 are shown by way of example in FIG. 1; the stimulation unit 11 can naturally, however, also have a different number of stimulation contacts. The electrode shaft and the stimulation contacts 25-28 are manufactured from a biocompatible material. Furthermore, the stimulation contacts 25-28 are electrically conductive, are for example produced from a metal and are located in direct electrical contact with the nerve tissue after the implanting. Each of the stimulation contacts 25-28 can preferably be controlled via its own feed line. Alternatively, two or more stimulation contacts 25-28 can also be connected to the same feed line. The stimulation contacts 25-28 can have any desired geometries; they can, for example, be round or rectangular or can extent circularly around the electrode shaft and can furthermore be arranged as desired with respect to one another.

Beside the stimulation contacts 25-28, each electrode can have a reference electrode whose surface may be larger than that of the stimulation contacts 25-28. The generator housing can e.g. also be used as a reference. The reference electrode is used to generate a reference potential in the stimulation of the nerve tissue. Alternatively, one of the stimulation contacts 25-28 can also be used for this purpose. Stimulation can i.e. take place either in a monopolar manner between an individual stimulation contact 25-28 and the reference electrode or in a bipolar manner between different stimulation contacts 25-28.

The measuring unit 12 includes one or more sensors which in particular make possible (i) a stimulus-induced reset of the phase of the pathological oscillatory activity and (ii) a detection of a decrease or increase in the amplitude of the pathological oscillatory activity.

Non-invasive sensors can be used as the sensors, e.g. electroencephalograph (EEG) electrodes, magnetic encephalograph (MEG) sensors and sensors for measuring local field potentials (LFPs). The neural activity can also be determined indirectly by measurement of the accompanying muscle activity by means of electromyography (EMG).

Alternatively, the sensors can be implanted in the body of the patient. Epicortical electrodes, deep brain electrodes for the measurement of e.g. local field potentials, subdural or epidural brain electrodes, subcutaneous EEG electrodes and subdural or epidural spinal marrow electrodes can, for example, serve as invasive sensors. The deep electrodes for measuring the local field potentials can also be combined construction-wise or can even be identical to the deep electrodes used for the stimulation.

Provision can by all means be made that the individual components of the apparatus 1, in particular the control and analysis unit 10, the stimulation unit 11 and/or the measuring unit 12, are separate from one another construction-wise. The apparatus 1 can therefore also be understood as a system.

The apparatus 1 can in particular be used for treating neurological or psychiatric diseases, e.g. Parkinson's disease, essential tremor, tremor resulting from multiple sclerosis as well as other pathological tremors, dystonia, epilepsy, depression, locomotor disorders, cerebellar diseases, obsessive compulsive disorders, dementia, Alzheimer's, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, cluster headache, general headache, neuralgia, ataxia, tic disorder or hypertension as well as further diseases which are characterized by pathologically increased neural synchronization.

The aforesaid diseases can be caused by a disorder of the bioelectric communication of neural assemblies which are connected in specific circuits. In this respect, a neural population continuously generates pathological neural activity and possibly a pathological connectivity associated therewith (network assembly). In this respect, a large number of neurons synchronously form action potentials, i.e. the participating neurons fire excessively synchronously. In addition, there is the fact that the pathological neural population has an oscillatory neural activity, i.e. the neurons fire rhythmically. In the case of neurological or psychiatric diseases, the mean frequency of the pathological rhythmic activity of the affected neural assemblies lies approximately in the range from 1 to 50 Hz, but can also be outside this range. In healthy people, the neurons fire qualitatively differently, however; e.g. in an uncorrelated manner.

The apparatus 1 is shown during a CR stimulation in FIG. 1. At least one neural population 30 in the brain 29 or in the spinal cord 29 of the patient has a pathologically synchronous and oscillatory neural activity as described above. The stimulation unit 11 stimulates the pathologically active neural population 30 in the brain 29 and/or in the spinal cord 29 with the electrical stimuli 22 either directly or the stimuli 22 are forwarded via the nervous system to the pathologically active neural population 30. The electrical stimuli 22 are designed such that the pathologically synchronous activity of the neural population 30 is desynchronized. A lowering of the coincidence rate of the neurons effected by the stimulation can result in a lowering of the synaptic weights and thus in an unlearning of the tendency to produce pathologically synchronous activity.

The electrical stimuli 22 administered in the CR stimulation effect a reset of the phase of neural activity of the neural activity of the stimulated neurons in the neural population 30. The phase of the stimulated neurons is set to or close to a specific phase value, e.g. 0°, (it is not possible in practice to set a specific phase value exactly; however, this is also not required for a successful CR stimulation) independently of the current phase value by the reset. The phase of the neural activity of the pathological neural population 30 is thus controlled by means of a direct stimulation. Since the pathological neural population 30 is stimulated at different sites via the stimulation contacts 25-28, the phase of the neural activity of the pathological neural population 30 at the different stimulation sites can be reset at different times. As a result, the pathological neural population 30 whose neurons were previously synchronous and active at the same frequency and phase is split into a plurality of subpopulations which are shown schematically in FIG. 1 and are marked by the reference numerals 31, 32, 33 and 34. For example, stimulation contact 25 stimulates subpopulation 31, stimulation contact 26 stimulates subpopulation 32, stimulation contact 27 stimulates subpopulation 33 and stimulation contact 28 stimulates subpopulation 34. Within each of the subpopulations 31-34, the neurons are still synchronous after the resetting of the phase and also still fire at the same pathological frequency, but each of the subpopulations 31-34 has the phase with respect to their neural activity which was enforced by the stimulation stimulus generated by the respective stimulation contact 25-28. This means that the neural activities of the individual subpopulations 31-34 still have an approximately sinusoidal curve with the same pathological frequency, but different phases, after the resetting of their phases.

Due to the pathological interaction between the neurons, the state with at least two subpopulations generated by the stimulation is unstable and the total neural population 30 fast approaches a state of complete desynchrononization in which the neurons fire without correlation. The desired state i.e. the complete desynchronization is thus not immediately present after the time-offset (or phase-shifted) application of the phase-resetting stimuli 22, but is usually adopted within a few periods or even in less than one period of the pathological frequency.

One theory for explaining the stimulation success is based on the fact that the ultimately desired desynchronization is only made possible by the pathologically increased interaction between the neurons. In this respect, a self-organization process is made use of which is responsible for the pathological synchronization. It has the effect that a division of an overall population 30 into subpopulations 31-34 with different phases is followed by a desynchronization. In contrast to this, no desynchronization would take place without a pathologically increased interaction of the neurons.

Furthermore, a reorganization of the connectivity of the disturbed neural networks can be achieved by the CR stimulation so that long-continuing therapeutic effects can be brought about. The obtained synaptic conversion is of great importance for the effective treatment of neurological or psychiatric diseases.

In the following, the calibration is described which is carried out by the apparatus 1 in order thus to determine the ideal stimulation sites and in particular the ideal stimulation parameters for the electrical CR stimulation.

An important aspect of the calibration comprises locating those stimulation contacts from a group of present stimulation contacts which are capable of effecting a phase reset of the pathological oscillation after the implanting into the brain or spinal cord of the patient. The pathological oscillation is e.g. measured by means (of the macrosignal) of the EEG; it corresponds at the micro-plane to a pathologically abnormal synchronization of the individual neurons within the affected neural population(s). The stimulation contacts via which a respective phase reset can be effected are further tested in that they do not result, when used pairwise as a CR stimulation, in an increase in the synchronization (i.e. in the amplitude of the pathological oscillation) and in that the total group of N (>2) stimulation contacts comprising only such effective pairs of stimulation contacts can be used for an effective CR stimulation, i.e. in that this CR stimulation has a desynchronizing effect so that the amplitude of the pathological oscillation drops. If N=2, only the desynchronizing effect of the pair of stimulation contacts is examined.

Provision can also be made that the step with the testing of the pairs of stimulation contacts is omitted and work is immediately continued with the testing of the desynchronizing effect of the N stimulation contacts.

The above-outlined procedure can be configured differently depending on the medical demands. Two variants will be described in the following for illustration.

Figure 2:
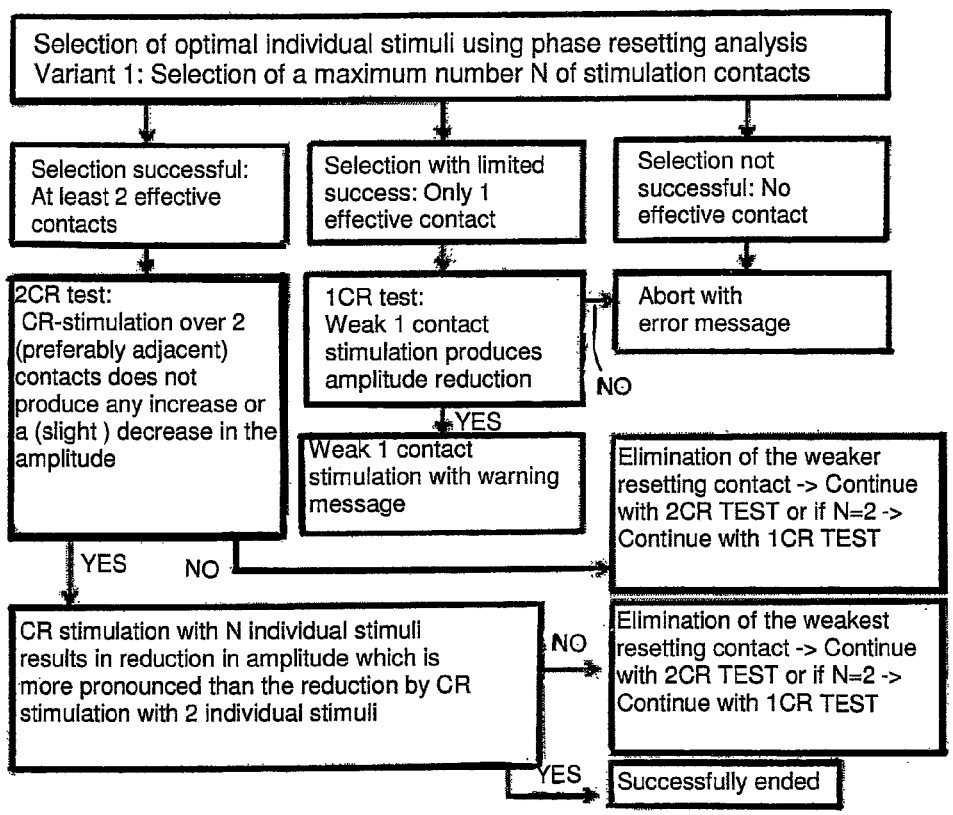
FIG. 2 a flowchart to illustrate the calibration of the apparatus shown in FIG. 1 in accordance with a first variant.

The steps carried out in accordance with a first variant are combined in the flowchart of FIG. 2. This variant is selected when as many effective stimulation contacts (i.e. stimulation contacts resetting the phase of pathological oscillation) as possible are to be selected. Those N stimulation contacts are selected from all present stimulation contacts which effect a phase reset of the pathological oscillation of brain activity (or of muscle activity). A subgroup of all (physically) present stimulation contacts can also be used. E.g. the upper, middle or lower third (lying at the electrode tip) of all stimulation contacts of an electrode can be selected. All those stimulation contacts can also be selected which are particularly promising—in accordance with additional information. Such additional information is e.g.: Information reconstructed from magnetic resonance examinations and/or computer tomograph examinations or with respect to the position of the electrode (together with stimulation contacts) in relation to the extent of the target zone to be stimulated or of a fiber tract to be stimulated. In addition, numerical simulations of computer models based thereon can be used as an indication for optimum stimulation contacts in order a priori to correspondingly restrict the stimulation contacts to be tested. Such additional information can, however, also be used only for a comparison with the functional testing. If e.g. the results of the functional testing correspond to the results of the anatomical reconstruction and dynamic computer simulation, the highest possible reliability of the calibration can be assumed.

First, the largest possible number N of stimulation contacts are selected from all present stimulation contacts or of an above-described subgroup which are able to reset the phase of the pathological oscillatory brain activity (or muscle activity). For this purpose, all stimulation contacts or the stimulation contacts of a subgroup are individually tested in that in a first step electrical stimuli are administered to the nerve tissue via each of these stimulation contacts. The stimulus strength is selected in this respect such that the stimuli are able to effect a phase reset of the pathological oscillation (which corresponds to a synchronous neural activity). If the initial stimulus strength was selected too low, the stimulus strength is increased via a corresponding setting of the stimulus parameters. The settable stimulus parameters include the amplitude of the individual pulses, the duration of the individual pulses, the pulse frequency of the pulse train and the number of the individual pulses in the pulse train. The testing of the stimuli parameters e.g. takes place by the phase resetting analysis described further below.

The analysis of the phase resetting of the pathological oscillation typically takes place by means of an ensemble of identical stimuli. Such an ensemble of electrical stimuli 40 which are applied after one another by each of the stimulation contacts is entered by way of example in FIG. 3 against the time t. To avoid entrainment phenomena, an interstimulus interval ISI between the individual stimuli 40 of sufficiently large and randomized length should be observed. The mean interstimulus interval should be long enough in comparison with the actual stimulus response so that the stimulus responses do not overlap and have completely decayed on administration of the subsequent stimulus 40.

The stimuli 40 are preferably bursts, i.e. brief radio frequency pulse trains (with the individual pulses being charge balanced). The parameters of the stimuli 40 greatly depend on the used electrode geometry and the stimulation contact surfaces and may not exceed the safety limit values familiar to the skilled person so that no tissue-damaging effects occur (cf. "Selection of stimulus parameters for deep brain stimulation" by A. M. Kuncel and W. M. Grill (published in Clin. Neurophysiol. 115, 2004, pages 2431 to 2441) and "Matching geometry and stimulation parameters of electrodes for deep brain stimulation experiments—numerical considerations" by U. Gimsa et al. (published in J. Neurosci. Methods 150, 2006, pages 212 to 227)). With specific dimensions of the stimulation contact surfaces currently used for clinical use, the amplitude of the individual pulses lies e.g. in the range from 0.2 mA to 4 mA, and in rare cases up to 6 mA. The duration of the individual pulses amounts to between 10 μm and 500 μs, and in particular between 60 μm and 200 μs. Between 1 and 20, and in particular between 3 and 9, individual pulses are located in a pulse train. The frequency within a pulse train amounts to between 80 Hz and 500 Hz, preferably between 100 Hz and 200 Hz, e.g. 130 Hz.

Using the measured signals recorded by the measuring unit in response to the application of the stimuli 40, the control and analysis unit determines whether the stimuli 40 applied by the individual stimulation contacts reset the phase of pathological, synchronized and oscillatory brain activity. In this respect, the control and analysis unit in a second step selects those stimulation contacts from the tested stimulation contacts which can reset the phase of pathological, synchronized and oscillatory brain activity (or muscle activity). Methods for examining such a phase reset are familiar to the skilled person.

One possibility familiar to the skilled person for the analysis of the phase reset comprises a phase resetting analysis by means of individually applied electrical stimuli (comprising an individual stimulus or a radio frequency pulse packet having an intra-burst frequency of preferably >100 Hz, e.g. 130 Hz, as will be described further below in connection with FIG. 6) as is described, for example, in the article "Stochastic phase resetting of two coupled phase oscillators stimulated at different times" by P. A. Tass (published in Physical Review E 67, 2003, pages 051902-1 to 051902-15) The phase resetting index is determined for this purpose (cf. equation 8, stimulus locking index for v=1). The phase used in this respect for calculating the phase resetting is e.g. determined using the Hilbert transformation from the signal which is determined using bandpass filtering or empirical mode decomposition and which represents the pathological oscillatory activity (the latter allows a parameter-independent determination of physiologically relevant modes in different frequency ranges in comparison with bandpass filtering, cf. "The empirical mode decomposition and the Hilbert spectrum for nonlinear and non-stationary time series analysis" by N. E. Huang et al. (published in Proceedings of the Royal Society of London Series A, 1998, Volume 454, pages 903 to 995); the combination of empirical mode decomposition with subsequent Hilbert transformation is called a Hilbert-Huang transformation, cf. "A confidence limit for the empirical mode decomposition and Hilbert spectral analysis" by N. E. Huang et al. (published in Proceedings of the Royal Society of London Series A, 2003, Volume 459, pages 2317 to 2345)). A phase reset is achieved when the phase resetting index exceeds the 99th percentile of the prestimulus distribution of the phase resetting index (cf. FIG. 4 in "Stochastic phase resetting of two coupled phase oscillators stimulated at different times" by P. A. Tass). If a stronger phase resetting effect is medically desirable, higher thresholds can also be selected, e.g. twice to three times the 99th percentile of the prestimulus distribution of the phase resetting index.

Alternatively to this data analysis, simpler data analysis processes can also be used which are able to approximate the detection of phase resetting with a sufficient precision in practice. E.g. averaging can take place simply via the ensemble of stimulus responses. A phase resetting is then approximately to be assumed when the maximum amount of the stimulus response exceeds the 99th percentile of the prestimulus distribution of the averaged response (or double or three times it) (cf. FIG. 6 in "Stochastic phase resetting of two coupled phase oscillators stimulated at different times" by P. A. Tass).

If no brain signal (LFP, EEG, MEG, time-dependent brainwaves or dipolar moments calculated by inverse processes from EEG and/or MEG signals) is used, but rather the muscle activity in the case of a patient with pathological tremor (trembling), a different preprocessing (familiar to the skilled person) of the signal of the muscle activity (e.g. the surface EMG) is to be carried out: The surface EMG is first high-pass filtered (e.g. >25 Hz) in order only to extract the burst activity, but to eliminate movement artifacts (in the frequency range of the pathological tremor, e.g. at 5 Hz). As the next step, the high-pass filtered signal is rectified, i.e. the modulus is taken. This signal is then further processed like a brain signal (LFP, EEG, MEG, time-dependent brainwaves or dipolar moments calculated by inverse processes from EEG and/or MEG signals).

The EEG and MEG signals are e.g. analyzed either directly after a corresponding preprocessing (e.g. elimination of artifacts such as blinking artifacts familiar to the skilled person) or after determining the underlying brainwaves by means of processes known to the skilled person for the backward calculation (using spatially distributed current densities or a plurality of dipoles). In the latter case, the temporal pattern of brainwaves or dipolar moments is analyzed. This allows a calibration to be carried out specifically coordinated with the phase resetting effect in one or more particularly relevant brain areas.

Figure 4:
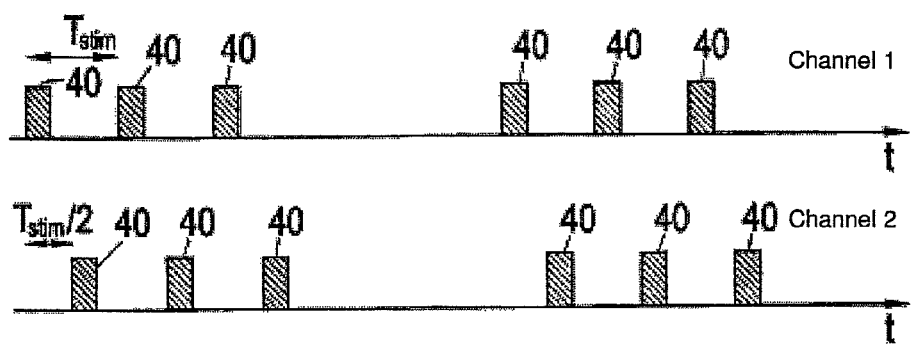
FIG. 4 a schematic representation of a CR stimulation using two adjacent stimulation contacts.

In a third step, a test is made whether the stimulation contacts are sufficiently far apart in comparison with the effect of the neural populations to be stimulated (to avoid stimulating two or more stimulation contacts of the same subpopulation. For this purpose, a respective 2 contact CR stimulation (2CR TEST) is carried out via adjacent stimulation contacts. FIG. 4 shows such a 2CR TEST having two adjacent stimulation contacts which each correspond to a channel. The electrical stimuli 40 are applied in a sequence periodically with the period $T_{stim}$ via each of the two stimulation contacts. In the present case, each sequence comprises three electrical stimuli 40; however, the sequences can also include further stimuli 40. A pause is observed after each sequence and the sequence is then repeated. The pause between the sequences can e.g. amount to a whole number multiple of the period $T_{stim}$. The time delay between the sequences of different channels furthermore amounts to $T_{stim}/2$, with it being possible to deviate from this value by e.g. up to ±5%, ±10% or ±20%. The period $T_{stim}$ is selected close to the mean period of the pathological oscillation. For example, the stimulation frequency $f_{stim}=1/T_{stim}$ in the 2CR TEST (and equally in the NCR TEST described further below), is either adapted to the frequency band to be desynchronized (e.g. with pathological synchronization in the delta band, a stimulation frequency located therein or even better in the lower half, that is e.g. 1.5 Hz) or—e.g. before the start of each testing quasi online—is adapted to the peak in the power spectrum of the pathological frequency band. In the latter case, the stimulation frequency $f_{stim}$ is selected such that this corresponds 1:1 to the peak frequency or—less preferably—to a smaller n:m multiple of the same (n, m are whole numbers and preferably <10). Furthermore, a literature value for the mean period of the pathological oscillation can be used and the period $T_{stim}$ used for the stimulation can differ from this literature value by e.g. up to ±5%, ±10% or ±20%. The stimulation frequency $f_{stim}$ typically lies in the range from 1 to 35 Hz.

The measured signals recorded in response to the 2CR TEST are analyzed by the control and analysis unit. The amplitude of the pathological oscillation should not be increased by the stimulation shown in FIG. 4; in the most favorable case, even a slight reduction can occur (corresponds to a weak desynchronization). In comparison with the total extent of the neural population, stimulation contacts which lie too densely can result in the most unfavorable case in an increase in the synchronization, i.e. in a growth of the amplitude of the pathological oscillation. This should be avoided. In this case, the stimulation contact which has a weak phase resetting effect in accordance with the initial examination is accordingly eliminated from such a pair of stimulation contacts which acts in a synchronizing manner in the 2CR TEST. The 2CR TEST is carried out for all adjacent pairs from the previously selected N stimulation contacts with an optionally subsequent elimination of unsuitable stimulation contacts and can thus be used so frequently until finally a group of N' N) stimulation contacts remains.

Figure 5:
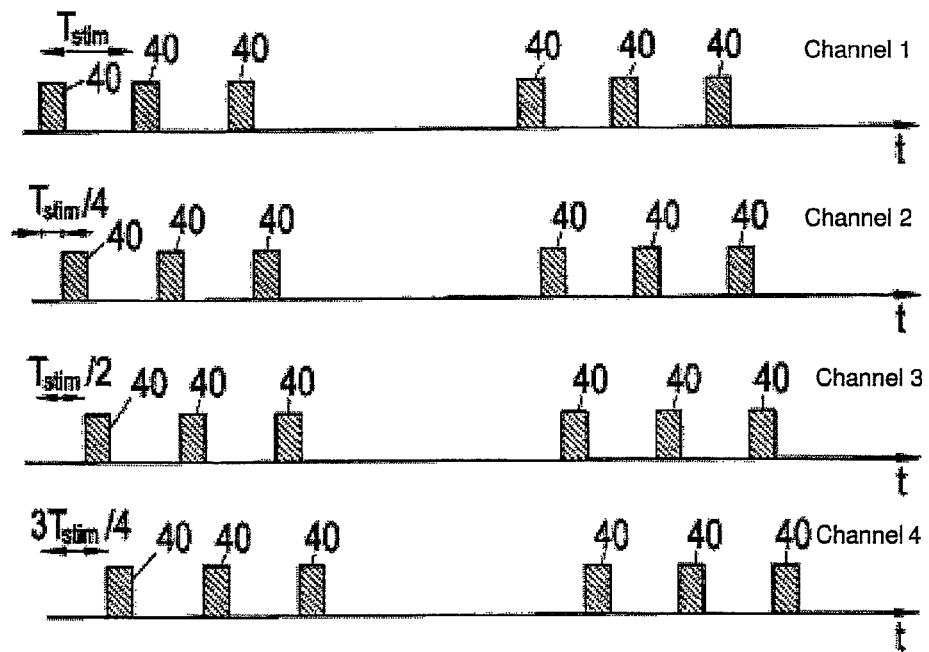
FIG. 5 a schematic representation of a CR stimulation using four stimulation contacts.

In the fourth step, a CR stimulation is carried out over all these N' stimulation contacts (NCR TEST) such as is shown e.g. in FIG. 5 for N'=4. In each of the four channels (each channel corresponds to an effective stimulation contact), the electrical stimulus 40 is applied periodically in a sequence with the period $T_{stim}$, where $T_{stim}$ here, as described above, also lies close to the mean period of the pathological oscillation (typically $f_{stim}=1/T_{stim}$ lies in the range from 1 to 35 Hz). In the present case, each sequence comprises three stimuli 40; however, the sequences can also include more stimuli 40. A specific pause is observed after each sequence and the sequence is then repeated. The time delay between the sequences of adjacent channels furthermore amounts to $T_{stim}/4$, since four passages are present. For the general case of N' channels, the time delay of adjacent channels would amount to $T_{stim}/N'$ (it is also possible to deviate from this value by e.g. up to ±5%, ±10% or ±20%).

If this CR stimulation suppresses the pathologically synchronous and oscillatory neural activity of the stimulated neurons and in particular has a desynchronizing effect (i.e. if the amplitude of the pathological oscillation falls significantly below the amplitude prior to the stimulation start; corresponding significance tests are familiar to the skilled person), these N' stimulation contacts are selected for treating the patient. If this is not the case, a less efficient stimulation contact has to be eliminated; and the procedure starts again with the 2CR TEST or continues with the 1CR TEST.

The 1CR TEST is used in the suboptimum case when only one stimulation contact is effective (i.e. effects a phase resetting). It is tested in this manner whether a weak one-contact CR stimulation (i.e. in comparison with the standard radio frequency stimulation carried out with an amplitude lower by the factor of 2 or—better—3), i.e. a periodic application of stimulation bursts, effects a significant reduction of the amplitude of the pathological oscillation. If this is the case, this variant can be selected as the treatment mode by the control and analysis unit. The control and analysis unit should, however, in any case deliver a warning in which it is made clear that the one-contact CR stimulation is clearly suboptimum. It has a much slower effect than a multichannel CR stimulation and brings about the risk of a synchronizing effect at high stimulation strengths.

If not even one single effective stimulation contact remains within the framework of the test procedure, the control and analysis unit delivers a corresponding error message and the test is aborted.

The first variant can—as already described—also be carried out with the condition that the maximum number of effective stimulation contacts is to be selected from a subset of stimulation contacts. The subset can e.g. be defined in a primarily apparatus-orientated manner (e.g. the upper or middle or lower third of all stimulation contacts) or by additional information, e.g. anatomical information (stimulation contacts which lie in the target zone in accordance with the imaging).

Figure 3:
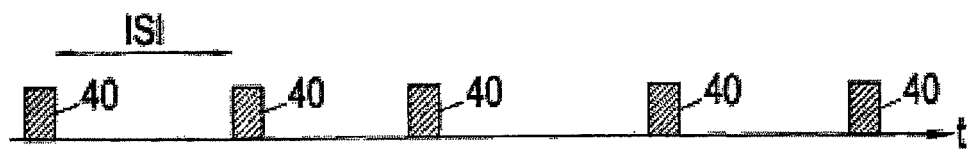
FIG. 3 a schematic representation of a stimulus sequence for the analysis of the phase reset effected by the stimuli.
Figure 6:
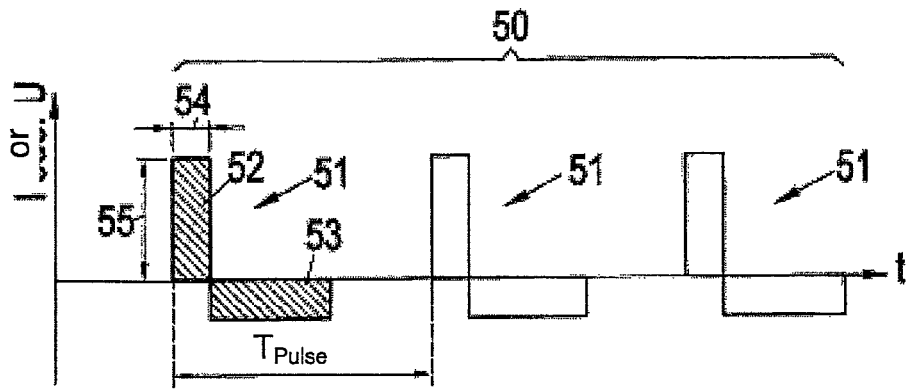
FIG. 6 a schematic representation of an electrical pulse train used for the stimulation.

FIG. 6 shows by way of example a pulse train 50 which can be used as an individual stimulus 40 in the stimulation processes shown in FIGS. 3, 4 and 5. The pulse train 50 can comprise 1 to 100, in particular 2 to 10, electrical charge-balanced single pulses 51 (in FIG. 6, 3 individual pulses 51 are shown by way of example). The individual pulses 51 are repeated within the pulse train 50 at a frequency $f_{pulse}=1/T_{pulse}$ in the range from 50 to 500 Hz, in particular in the range from 100 to 150 Hz. The individual pulses 51 can be current-controlled or voltage-controlled pulses which are composed of an initial pulse portion 52 and a pulse portion 53 following it and flowing in the opposite direction, with the polarity of the two pulse portions 52 and 53 also being able to be swapped over with respect to the polarity shown in FIG. 6. In addition, a pause of a length of up to 20 ms can be inserted between both pulse portions 52, 53. The duration 54 of the pulse portion 52 lies in the range between 1 µs and 500 µs. The amplitude 55 of the pulse portion 52 lies in the case of current-controlled pulses in the range between 0 mA and 25 mA and in the case of voltage-controlled pulses in the range from 0 to 20 V. The amplitude of the pulse portion 53 is smaller than the amplitude 55 of the pulse portion 52. In turn the duration of the pulse portion 53 is longer than that of the pulse portion 52. The pulse portions 52 and 53 are ideally dimensioned such that the charge which is transferred by them is of equal size in both pulse portions 52 and 53, i.e. the areas drawn hatched in FIG. 6 are of equal size. Accordingly, just as much charge is introduced into the tissue by an individual pulse 51 as is removed from the tissue.

The rectangular shape of the individual pulses 51 shown in FIG. 6 represents an ideal form. There is a deviation from the ideal rectangular shape in dependence on the quality of the electronics generating the individual pulses 51.

Instead of electrical individual pulses or pulse trains, differently configured electrical stimuli can also be used in the CR stimulation, e.g. time-continuous stimulus patterns. The above-described signal shapes and their parameters are therefore only to be understood by way of example. Provision can by all means be made that there is a deviation from the above-indicated signal shapes and their parameters.

Figure 7:
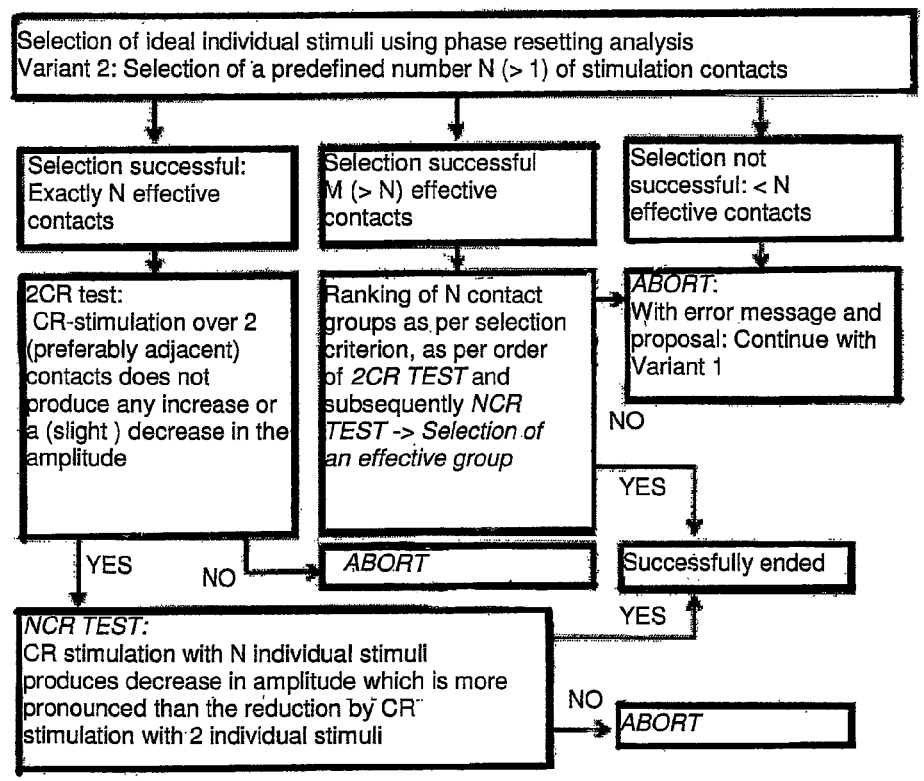
FIG. 7 a flowchart to illustrate the calibration of the apparatus shown in FIG. 1 in accordance with a second variant.

In the following, a second calibration variant will be described for determining the optimum stimulus parameters and stimulation sites for the electrical CR stimulation whose essential steps are combined in the flowchart of FIG. 7.

With a corresponding electrode geometry, e.g. with a presence of a very large number of stimulation contacts, it can be medically advantageous not to carry out the CR stimulation via as many stimulation contacts as possible, but rather via an ideal number of stimulation contacts. In this case, the desired number N of stimulation contacts is selected at the start of the calibration. If exactly N stimulation contacts effect a phase resetting of the pathological oscillation, an examination is made (as in the first variant) in a 2CR test and in a subsequent NCR test whether the CR stimulation, applied over all N stimulation contacts, results in a significant reduction in the amplitude of the pathological oscillation.

If M (>N) stimulation contacts effect a phase reset of the pathological oscillation, a ranking of possible N contact groups is prepared in accordance with a selection criterion.

In accordance with a first selection criterion, the N stimulation contacts furthest remote from one another are selected from the M stimulation contacts. If two or more possibilities are given, those stimulation contacts having the largest cumulative phase resetting index (maximum value summed over all stimulation contacts) are selected.

In accordance with a second selection criterion, those N stimulation contacts are selected from M stimulation contacts which effect the greatest phase resetting.

In accordance with a third selection criterion, those N stimulation contacts are selected from M stimulation contacts which have the greatest overlap with the condition (of the target zone to be stimulated) determined by an anatomical reconstruction (and optionally an additional dynamic computer simulation). Those N stimulation contacts can e.g. be selected which are closest to the target zone.

In accordance with this ranking (analog to the above-described procedure), the ideal group with N stimulation contacts is determined by means of the 2CR TEST and the following NCR TEST. If this is not possible, either a one-contact CR stimulation or no CR stimulation is selected as the best possible therapy.

Figure 8:
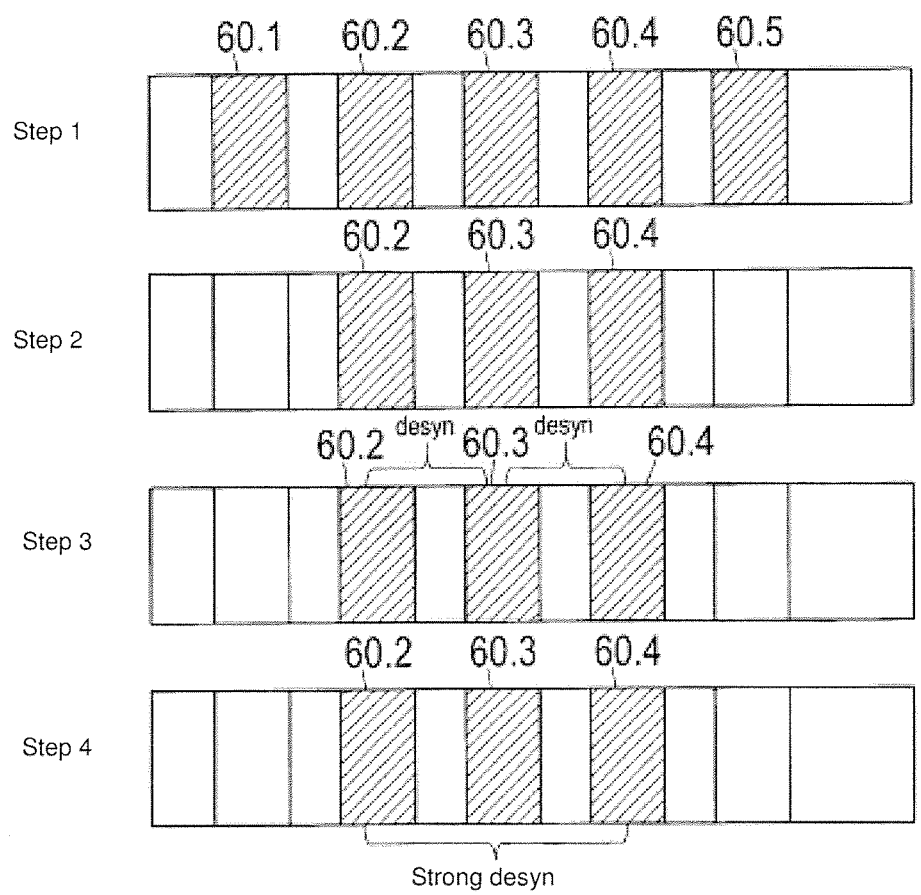
FIG. 8 a flowchart to illustrate the calibration for an electrode with circular stimulation contacts.

FIGS. 8 and 9 illustrate the calibration procedure in accordance with the above-described first variant at two different electrode geometries.

The electrode shown schematically in FIG. 8 has five circular stimulation contacts 60.1-60.5. The electrode tip (not drawn in any more detail) is at the left in the representation of FIG. 8. The horizontal dimension shows the longitudinal orientation of the electrode. The outer surface (i.e. the contact surface with the nerve tissue) of the electrode is cut open (i.e. the upper and lower longitudinal edges were fused before the cutting open).

In step 1, electrical stimuli are administered to the nerve tissue via each of the stimulation contacts 60.1-60.5. The control and analysis unit determines the stimulation contacts which effect an effective phase reset of the pathological oscillation in step 2 using the measured signals records in this respect, e.g. EEG and/or MEG signals. In the example of FIG. 8, the stimulation contacts 60.2-60.4 satisfy this criterion. The 2CR TEST is carried out in step 3 using these three stimulation contacts. The CR stimulations carried out in the 2 CR TEST using two respective adjacent stimulation contacts, i.e. CR stimulations with the pairs 60.2/60.3 and 60.3 and 60.3/60.4, does not result in any increase in the amplitude of the pathological oscillation. Subsequently, in step 4, the NRC TEST is therefore carried out with all three stimulation contacts 60.2-60.4. The CR stimulation carried out within the framework of this test with the three stimulation contacts 60.2-60.4 has a highly desynchronizing effect on the stimulated neural population. The calibration procedure accordingly delivers as the result the stimulation contacts 60.2-60.4 with which ideal results can be achieved in the following CR therapy.

FIG. 9 schematically shows an electrode having 16 circular stimulation contacts 70.1-70.16, with the electrode tip (not drawn in any more detail) being at the left in the representation of FIG. 9. The horizontal dimension shows the longitudinal orientation of the electrode. The outer surface (i.e. the contact surface with the nerve tissue) of the electrode is cut open. I.e. the upper and the lower longitudinal edges were fused before the cutting open.

In step 1, the calibration procedure is carried out on all present stimulation contacts 70.1-70.16 (and no subgroup thereof). In step 2, the control and analysis unit determines the stimulation contacts which effect an effective phase reset of the pathological oscillation by means of the EEG and/or MEG signals recorded during step 1. In the present example, they are the stimulation contacts 70.2-70.6 and 70.12-70.14. In step 3, the 2CR TEST is carried out using all adjacent pairs of the stimulation contacts selected in step 2. In this respect, horizontal adjacent pairs (e.g. 70.3/70.4), vertical adjacent pairs (e.g. 70.4/70.12) and diagonal adjacent pairs (e.g. 70.3/70.12) are tested. In the present embodiment, the stimulation contact 70.6 is eliminated in this respect. Subsequently, in step 4, the NCR TEST is carried out with the remaining stimulation contacts 70.2-70.5 and 70.12-70.14 and it is shown that a CR stimulation using these stimulation contacts results in a strong desynchronization of the stimulated neural population.

The clinical testing (e.g. the observation of the effect of the stimulation of the cardinal symptoms of Parkinson's, that is of tremor, rigor and akinesia) is replaced by such objective examinations to be carried out systematically. Subjective impressions, and in part impressions only reliable with restrictions, of the evaluating physician are thereby replaced by an electrophysiologically based measurement of the stimulus responses of the brain for the calibration of the optimum stimulation parameters and stimulation sites.

Different types of CR stimulation can be used for the subsequent therapy. One possibility comprises an "N from N" CR stimulation, i.e. individual stimuli 40 from all N selected stimulation contacts are applied per stimulation cycle $T_{stim}$ as in FIG. 5 (for N=4). Alternatively, an "L from N" CR stimulation (where L<N) can also be carried out in which L from N stimulation contacts are selected, e.g. in a randomized manner, per stimulation cycle $T_{stim}$ and the stimuli 40 from these are applied. In this manner, a larger spatial variability can be generated.

Further variations of the CR stimulation using four stimulation contacts (N=4) determined using the calibration procedure are shown in FIGS. 10 and 11.

FIG. 10 shows a pause which can be provided between the application of the stimuli 40 and during which no stimulation takes place. Such pauses can be selected to be of any length and can in particular amount to a whole-number multiple of the period $T_{stim}$. Furthermore, the breaks can also be observed after any desired number of stimulations. E.g. a stimulation can be carried out during P mutually following periods of the length $T_{stim}$ and subsequently a pause can be observed during Q periods of the length $T_{stim}$ without stimulation, where P and Q are small whole numbers, e.g. in the range from 1 to 20. This scheme can either be continued periodically or modified stochastically and/or deterministically, e.g. chaotically.

A further possibility to deviate from the strictly periodic stimulation pattern shown in FIG. 5 comprises varying the time sequence of the individual stimuli 40 stochastically or deterministically or in mixed stochastic/deterministic form. FIG. 11 shows that the order in which the individual stimulation contacts apply the stimuli 40 is varied per period $T_{stim}$ (or also in other time steps). This variation can take place stochastically or deterministically or in a mixed stochastic/deterministic manner.

The randomization shown in FIG. 11 can be combined with the stimulation form shown in FIG. 10. For example, a repeat randomization can be carried out in each of the P mutually following stimulation time periods of the length $T_{stim}$ or a randomization takes place after each pause of the length $Q \times T_{stim}$ and the order in which the stimulation contacts apply the stimuli 40 remains constant within the P following stimulation time periods.

Furthermore, it is possible to deviate from the strictly periodic stimulation pattern shown in FIG. 5 in that the time delay between two mutually following stimuli 40 is not always of the same amount. Provision can be made that the time intervals between the individual stimuli 40 are selected as different. Furthermore, the delay times can also be varied during the treatment of a patient. The delay times can also be adjusted with reference to the physiological signal transit times.

Figure 12:
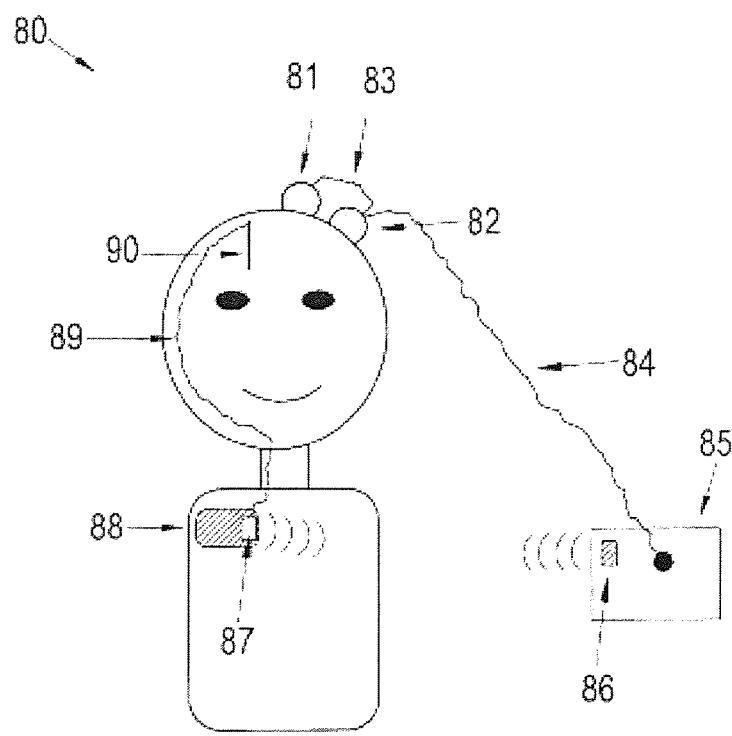
FIG. 12 a schematic representation of a further apparatus for an EEG-based calibration of a CR stimulation.

FIG. 12 schematically shows an apparatus 80 for an EEG-based calibration of the CR stimulation, applied via implanted brain electrodes (e.g. deep electrodes), for the treatment of neurological and psychiatric diseases with pathologically increased neural synchronization, e.g. Parkinson's, dystonia, pathological tremors (e.g. essential tremor), epilepsies, Gilles de la Tourette syndrome, obsessive compulsive disorders, depressions, Alzheimer's, dementia, serious addiction diseases and very serious personality disorders. Non-invasively fixed EEG electrodes 81, 82 measure the EEG stimulus responses and transmit the respective EEG responses via cables 83, 84 to the central control/amplifier and analysis unit 85. The latter communicates bidirectionally via a corresponding transmission and reception unit 86 telemetrically with the telemetric transmission and reception unit 87 of the implanted generator 88. The latter is connected via a lead-away cable 89 to one or more implanted deep electrodes 90. Electrical test stimuli are administered via the deep electrode 90. The control signals used for this purpose are generated by the generator 88—in accordance with the telemetrically transmitted values from the control/amplifier and analysis unit 85. The latter carries out the data analysis of the EEG stimulus responses.

Instead of an implanted generator and a non-implanted control/amplifier and analysis unit telemetrically communicating with the generator, the control/amplifier and analysis unit can also be integrated into the generator housing. The control/amplifier and analysis unit can in this case initiate the running of a standardized program of test stimuli and can (approximately) determine the stimulation times from the EEG artifacts. In another variant, the generator is directly connected to the implanted deep electrode via a led-out cable. The disadvantage in this respect is that such a leading out brings about a risk of infection such that the leading out is only carried out in accordance with current practice (in accordance with corresponding study results) in the first 10 days after the electrode implanting in many small clinical centers. In this time, there is, however, still an edema in some of the patients as a consequence of the implanting of the macroelectrode in the front region of the electrode (the edema decaying in the further course) so that the neural population can there have both a changed spontaneous behavior (e.g. much less or even no pathologically synchronous activity) and changed stimulus responses.

The invention claimed is:

1. An apparatus for stimulating neurons with a pathologically synchronous and oscillatory neural activity, comprising:
   a stimulation unit having a plurality of stimulation contacts for stimulating neurons in at least one of a brain and a spinal cord of a patient using electrical stimuli;
   a measuring unit for recording measured signals, the measured signals reproducing a neural activity of the stimulated neurons; and
   a control and analysis unit for controlling the stimulation unit and for analyzing the measured signals, wherein the control and analysis unit is configured to:
      control the stimulation unit to apply the electrical stimuli using the stimulation contacts;
      select the stimulation contacts, whose electrical stimuli effect a phase reset of the pathologically synchronous and oscillatory neural activity of the respective stimulated neurons based on the measured signals recorded in response to the application of the electrical stimuli;
      control the stimulation unit such that the selected stimulation contacts apply phase resetting stimuli pairwise with a time offset;
      determine, based on measured signals recorded by the measuring unit in response to application of the phase resetting stimuli, whether the applied phase resetting stimuli suppress the pathologically synchronous and oscillatory neural activity of the respective stimulated neurons;
      determine, based on the measured signals recorded in response to the phase-resetting stimuli by a pair of stimulation contacts, whether the phase resetting stimuli effect an increase in the pathologically synchronous and oscillatory activity of the neurons; and
      select the stimulation contacts that are determined to suppress the pathologically synchronous and oscillatory neural activity of the respective stimulated neurons.

2. The apparatus in accordance with claim 1, wherein the control and analysis unit is further configured to stop
   one of the two stimulation contacts from applying the phase-resetting stimuli if the phase-resetting stimuli applied with a time offset by the pair of stimulation contacts effect an increase in the pathologically synchronous and oscillatory activity of the neurons.

3. The apparatus in accordance with claim 2, wherein the control and analysis unit is further configured to stop stimulation by
   the stimulation contacts that effect a weaker phase reset of the neural activity of the stimulated neurons by the phase resetting stimuli.

4. The apparatus in accordance with claim 1, wherein the stimulation contacts of a pair of stimulation contacts are arranged adjacent to one another.

5. The apparatus in accordance with claim 1, wherein the control and analysis unit is configured to select N stimulation contacts from a number M of stimulation contacts with which a phase reset of the pathologically synchronous and oscillatory neural activity of the stimulated neurons can be achieved
   which lie furthest remote from one another; and/or
   which effect the greatest phase reset of the neural activity of the stimulated neurons by means of the phase resetting stimuli; and/or
   which have the greatest overlap with the target zone in the brain and/or spinal cord of the patient.

6. A method of stimulating neurons with a pathologically synchronous and oscillatory neural activity, the method comprising:
   administering electrical stimuli to a patient by a plurality of stimulation contacts, wherein the stimuli stimulate neurons in at least one of a brain and a spinal cord of the patient;
   recording measured signals that reproduce a neural activity of the stimulated neurons;
   selecting, based on the measured signals, the stimulation contacts whose stimuli effect a phase reset of the pathologically synchronous and oscillatory neural activity of the stimulated neurons;
   controlling the selected stimulation contacts to apply the phase resetting stimuli pairwise with a time offset;
   recording measured signals that reproduce the neural activity of the stimulated neurons; and
   determining, based on the measured signals whether the applied phase resetting stimuli suppress the pathologically synchronous and oscillatory neural activity of the respective stimulated neurons;

determining, based on the measured signals, whether the phase resetting stimuli applied with a time offset by the pair of stimulation contacts effect an increase in the pathologically synchronous and oscillatory activity of the neurons selecting the stimulation contacts that are determined to suppress the pathologically synchronous and oscillatory neural activity of the respective stimulated neurons.

7. The method in accordance with claim 6, further comprising stopping application of the phase-resetting stimuli by one of the two stimulation contacts if the phase-resetting stimuli applied with a time offset by the pair of stimulation contacts effect an increase in the pathologically synchronous and oscillatory activity of the neurons.

8. The method in accordance with claim 7, further comprising stopping application of the phase-resetting stimuli by the stimulation contacts that effect a weaker phase reset of the neural activity of the stimulated neurons by the phase resetting stimuli.

9. The method in accordance with claim 6, wherein the stimulation contacts of a pair of stimulation contacts are arranged adjacent to one another.

10. The method in accordance with claim 6, further comprising selecting N stimulation contacts are selected from a number M of stimulation contacts with which a phase reset of the pathologically synchronous and oscillatory neural activity of the stimulated neurons can be achieved which lie furthest remote from one another; and/or which effect the greatest phase reset of the neural activity of the stimulated neurons by means of the phase resetting stimuli; and/or which have the greatest overlap with the target zone in the brain and/or spinal cord of the patient.

* * * * *